United States Patent
Baxter

(10) Patent No.: US 10,807,924 B1
(45) Date of Patent: Oct. 20, 2020

(54) METHODS FOR SEPARATING COMPONENTS

(71) Applicant: NewVistas Capital, LLC, Provo, UT (US)

(72) Inventor: Larry Baxter, Orem, UT (US)

(73) Assignee: Hall Labs LLC, Provo, UT (US)

( * ) Notice: Subject to any disclaimer, the term of this patent is extended or adjusted under 35 U.S.C. 154(b) by 0 days.

(21) Appl. No.: 16/532,474

(22) Filed: Aug. 5, 2019

(51) Int. Cl.
  *C07C 7/04* (2006.01)
  *B01D 3/14* (2006.01)
  *B01D 3/32* (2006.01)

(52) U.S. Cl.
  CPC ............. *C07C 7/04* (2013.01); *B01D 3/141* (2013.01); *B01D 3/146* (2013.01); *B01D 3/32* (2013.01)

(58) Field of Classification Search
  CPC .......... C07C 7/04; B01D 3/141; B01D 3/146; B01D 3/32
  See application file for complete search history.

(56) References Cited

U.S. PATENT DOCUMENTS

| 4,720,294 A | * | 1/1988 | Lucadamo | C07C 7/04 62/627 |
| 5,335,504 A | * | 8/1994 | Durr | B01D 3/141 62/632 |

\* cited by examiner

*Primary Examiner* — Brian A McCaig

(57) ABSTRACT

Method for concentrating components through a distillation column are disclosed. A process stream is provided containing hydrocarbons, carbon dioxide, and water. The process stream is passed into the distillation column at a bottom portion of the distillation column. The process stream is fractionally distilled in the distillation column, forming an overhead vapor stream, a middle fluid stream, and a bottoms liquid stream. The middle fluid stream is removed from a middle location of the distillation column. The bottoms liquid stream is removed from the distillation column. The overhead vapor stream is removed from the distillation column. The middle fluid stream consists of a first portion of the carbon dioxide and a first portion of the hydrocarbons. The bottoms liquid stream consists of a second portion of the hydrocarbons as a first phase and substantially all the water as a second phase.

20 Claims, 2 Drawing Sheets

METHODS FOR SEPARATING COMPONENTS

GOVERNMENT INTEREST STATEMENT

This invention was made with government support under DE-FE0028697 awarded by the Department of Energy. The government has certain rights in the invention.

TECHNICAL FIELD

The methods and processes described herein relate generally to fractional distillation.

BACKGROUND

Separation of fluid components is often energy intensive or complex. Separating components can be done, but the higher the purity required, the more unit operations are typically required. Alternatives to traditional fluid separation techniques are required.

SUMMARY

In a first aspect, the disclosure provides a method for concentrating components through a distillation column. A process stream is provided containing hydrocarbons, carbon dioxide, and water. The process stream is passed into the distillation column at a bottom portion of the distillation column. The process stream is fractionally distilled in the distillation column, forming an overhead vapor stream, a middle fluid stream, and a bottoms liquid stream. The middle fluid stream is removed from a middle location of the distillation column. The bottoms liquid stream is removed from the distillation column. The overhead vapor stream is removed from the distillation column. The middle fluid stream consists of a first portion of the carbon dioxide and a first portion of the hydrocarbons. The bottoms liquid stream consists of a second portion of the hydrocarbons as a first phase and substantially all the water as a second phase.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 3:
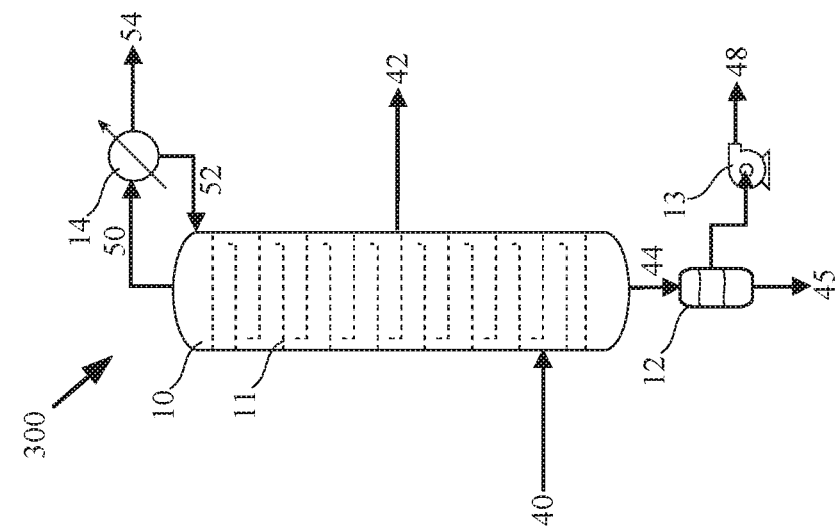
FIG. 3 is a flow diagram of a method for separating components through a distillation column that may be used in one embodiment of the present invention.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "distillation column" refers to any unit operation that separates components of a fluid by distillation.

As used herein, "C3+" hydrocarbons refers to hydrocarbons with three or more carbon atoms.

As used herein, "natural gas" refers to a gas containing primarily methane, and that may optionally have other ingredients, such as ethane, propane, butane and carbon dioxide.

Separations of components in distillation columns is often complicated by the presence of components that are miscible or have similar boiling points. For example, propane has some solubility in water and heptane has a boiling point nearly identical to water. Streams of hydrocarbons contaminated with carbon dioxide and water add to the overall complications. The present invention discloses methods for separating a process stream containing hydrocarbons, carbon dioxide, and water through a distillation column. The process stream is passed into the distillation column near the bottom of the column, preferably below the column trays or packing. The process stream is then fractionally distilled to form an overhead vapor stream, a middle fluid stream, and a bottoms liquid stream. In a preferred embodiment, the incoming process stream is at a temperature that causes it to at least partially flash and negating the need for a reboiler. The middle fluid stream is removed from a middle location of the distillation column. In a preferred embodiment, 90 wt % of the carbon dioxide entering with the process stream leaves with the middle fluid stream as a liquid at a 98 wt % purity. The balance of the middle fluid stream is typically a mixture of methane, ethane, and propane, in descending order of concentration. The bottoms liquid stream is removed from the distillation column. In a preferred embodiment, the bottoms liquid stream is primarily C3+ and water, with some carbon dioxide. As a first embodiment for separating the water and the C3+, a solvent, typically a light alcohol such as methanol or ethanol, a ketone, such as acetone, an aldehyde, or other polar organic molecules are added to the process stream. The solvent and the water form a separate phase from the C3+ in the bottom of the distillation column, where they are gravity separated. The C3+ can be decanted off the top of the solvent/water mixture in the bottom of the distillation column, or the two phases can be separated in a dedicated separations vessel. As a second embodiment, the water can be allowed to freeze in the bottom of the distillation column and solid-liquid separation techniques can be used to separate the water ice from the C3+ and any carbon dioxide. The overhead vapor stream is removed from the distillation column as a natural gas stream and consists primarily of methane with some ethane and carbon dioxide. In some embodiments, light gases such as nitrogen and hydrogen sulfide may also be present.

Figure 1:
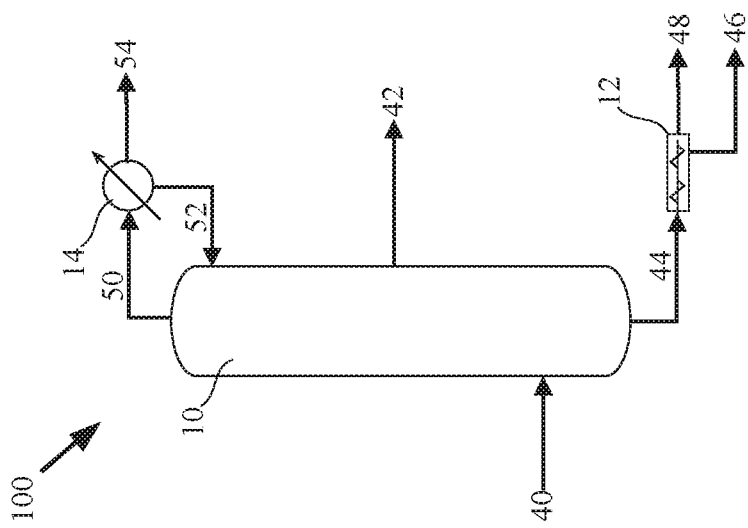
FIG. 1 is a flow diagram of a method for separating components through a distillation column that may be used in one embodiment of the present invention.

Now referring to the figures, FIG. 1 is a flow diagram of a method for separating components through a distillation column at 100 that may be used in one embodiment of the present invention. A distillation column 10 has a condenser 14. A process stream 40 in this embodiment consists of hydrocarbons, water, and carbon dioxide and is a mixture of a liquid phase and a gas phase. In this embodiment, the amount of carbon dioxide is preferably under 98 wt % and more preferably less than 93 wt %. Typically, the water in the process stream is at saturated conditions. The process stream is passed into the distillation column 10 where a portion of the liquid stream vaporizes and joins the gas phase to ascend the column against a recycled overhead stream 52. The overhead vapor stream 50 formed passes through condenser 14 producing the recycled overhead stream 52 and a product vapor stream 54. The product vapor stream consists primarily of methane, with some ethane, carbon dioxide, and light gases. A portion of the descending recycled overhead stream 52 is drawn from a middle portion of the distillation column 10 as middle fluid stream 42. In this embodiment, the middle fluid stream 42 is a liquid consisting of primarily carbon dioxide. In some embodiments, the middle fluid stream 42 is a gas. The portion of the recycled overhead stream 52 that is not drawn from the middle portion of the distillation column 10 descends the distillation column 10 to join the liquid phase to become a bottoms stream 44. The bottoms stream 44 consists primarily of C3+ hydrocarbons and water, with minor amounts of carbon dioxide. In this embodiment, the pressure and temperature of the column are low enough to cause the water to freeze to water ice, thereby forming a solid phase separate from the C3+ liquid phase. The two phases are removed as a slurry stream 44 and fed to a screw filter press 12 where the water ice stream 48 is separated from the liquid C3+ stream 46. In a preferred embodiment, over 99% of the water is removed in this step. In a most preferred embodiment, over 99.6% of the water is removed in this step. In this embodiment, the condenser is operated above the freezing point of the overhead vapor stream, keeping the CO2 from freezing, but approaching the temperature at which the carbon dioxide freezes. In a preferred embodiment, this is within 5° C. In a more preferred embodiment, this is within 3° C. In an even more preferred embodiment, this is within 2° C. In a most preferred embodiment, this is within 1° C. In this embodiment, no reboiler is provided as the incoming stream is warm enough that flashing into the distillation column 10 produces all the vapor needed for separations. In this embodiment, the column pressure is operated below the supercritical transition point. In a preferred embodiment, this is operated within 3 bar below the supercritical transition point. In a more preferred embodiment, this is operated between 5 bar and 3 bar below the supercritical transition point.

Figure 2:
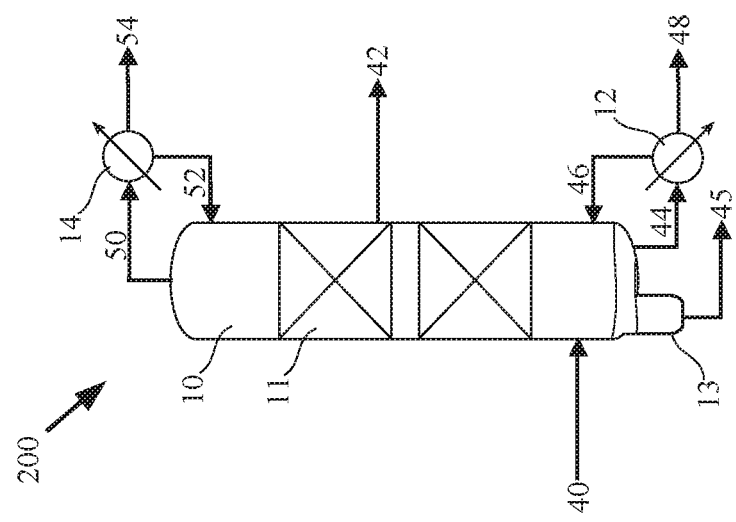
FIG. 2 is a flow diagram of a method for separating components through a distillation column that may be used in one embodiment of the present invention.

FIG. 2 is a flow diagram of a method for separating components through a distillation column at 200 that may be used in one embodiment of the present invention. A distillation column 10 has a condenser 14, a reboiler 12, and a boot 13. A process stream 40 consists of hydrocarbons, water, and carbon dioxide with an added polar solvent. The process stream is passed into the distillation column 10 where a portion of the process stream vaporizes and joins a recycled bottoms stream 46 to ascend the column against a recycled overhead stream 52 through packing 11. Packing is preferable to trays to avoid flooding or weeping. The overhead vapor stream 50 formed passes through condenser 14 producing the recycled overhead stream 52 and a product vapor stream 54. The product vapor stream consists primarily of methane, with some ethane and carbon dioxide. A portion of the recycled overhead stream 52 is drawn from a middle portion of the distillation column 10 as a middle fluid stream 42. In some embodiments, the middle fluid stream 42 is a gas. The portion of the recycled overhead stream 52 that is not drawn from the middle portion of the distillation column 10 descends the distillation column 10 to join any of the process stream 40 that did not flash in the bottom of the distillation column 10. The solvent added to the process stream is part of this bottoms liquid and is miscible in and mixes with the water to make a second phase that is immiscible with the primarily C3+ first phase. The second phase settles below the first phase and is drawn off as solvent/water stream 45 while the first phase is drawn off as bottoms liquid stream 44. The bottoms liquid stream 44 goes through reboiler 12 with a portion returning as recycled bottoms stream 46 and a portion becoming the bottoms product stream 48.

FIG. 3 is a flow diagram of a method for separating components through a distillation column at 300 that may be used in one embodiment of the present invention. A distillation column 10 has a condenser 14, a decanting vessel 12, and a pump 13. A process stream 40 consists of hydrocarbons, water, and carbon dioxide with an added solvent. The process stream is passed into the distillation column 10 where a portion of the process stream vaporizes and ascends the column against a recycled overhead stream 52 through trays 11. The overhead vapor stream 50 formed passes through condenser 14 producing the recycled overhead stream 52 and a product vapor stream 54. The product vapor stream consists primarily of methane, with some ethane and carbon dioxide. A portion of the recycled overhead stream 52 is drawn from a middle portion of the distillation column 10 as a middle fluid stream 42. The portion of the recycled overhead stream 52 that is not drawn from the middle portion of the distillation column 10 descends the distillation column 10 to join any of the process stream 40 that did not flash in the bottom of the distillation column 10. The solvent added to the process stream is part of this bottoms liquid stream 44 and is miscible in and mixes with the water to make a second phase that is immiscible with the primarily C3+ first phase. The bottoms stream 44 passes into the decanting vessel 12 where the second phase settles below the first phase and is drawn off as solvent/water stream 45 while the first phase is drawn off by pump 13 as bottoms liquid stream 48.

Figure 4:
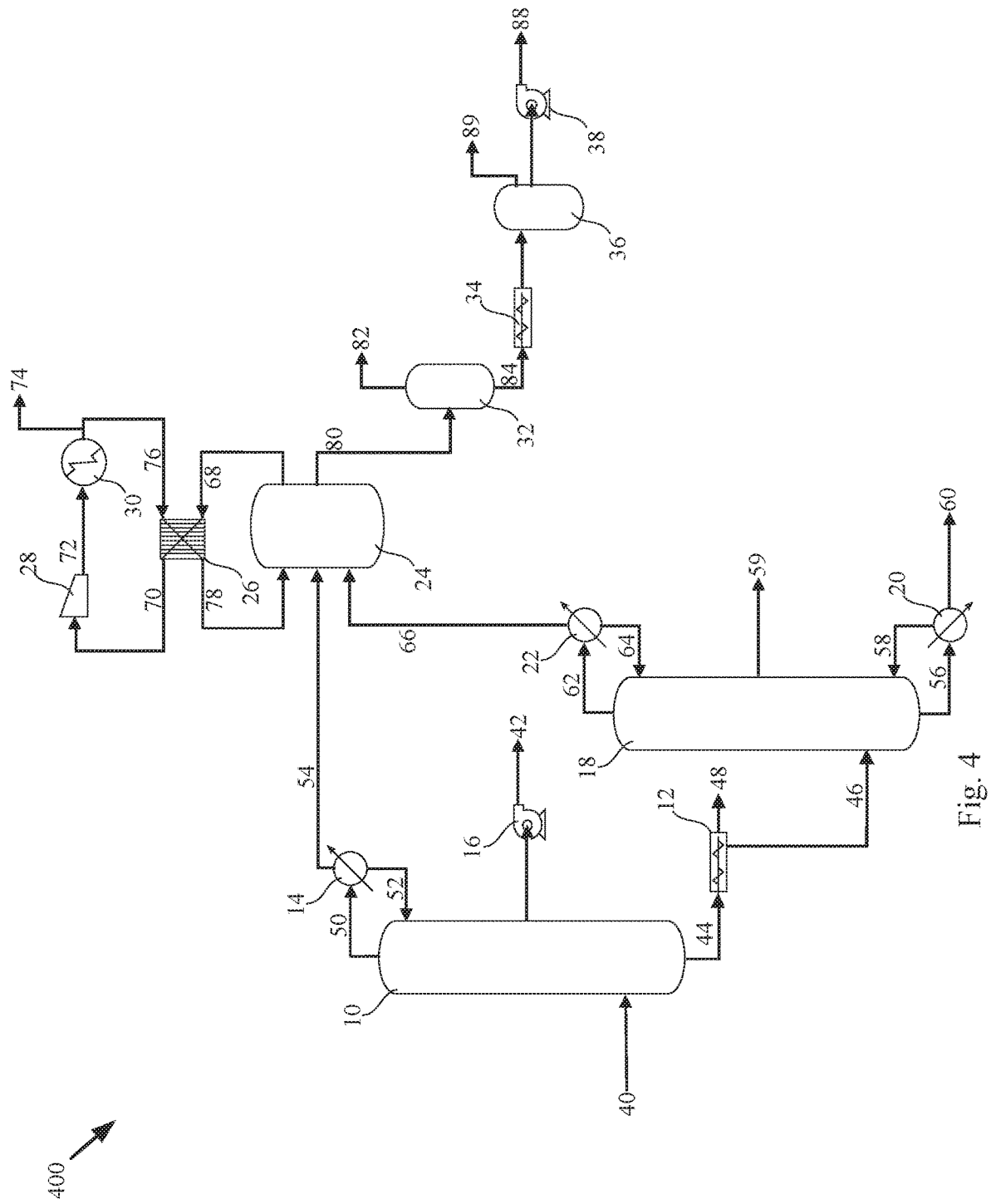
FIG. 4 is a flow diagram of a method for separating components through a distillation column and other unit operations that may be used in one embodiment of the present invention.

FIG. 4 is a flow diagram of a method for separating components through a distillation column and other unit operations at 400 that may be used in one embodiment of the present invention. A distillation column 10 has a condenser 14. A process stream 40 consists of hydrocarbons, water, and carbon dioxide and is a mixture of a liquid phase and a gas phase. The process stream is passed into the distillation column 10 where a portion of the liquid stream vaporizes and joins the gas phase to ascend the column against a recycled overhead stream 52. The overhead vapor stream 50 formed passes through condenser 14 producing the recycled overhead stream 52 and a product vapor stream 54. The product vapor stream consists primarily of methane, with some ethane, carbon dioxide, and light gases. A portion of the descending recycled overhead stream 52 is drawn from a middle portion of the distillation column 10 by pump 16 as middle fluid stream 42. The middle fluid stream 42 is a liquid consisting of about 98 wt % carbon dioxide with minor amounts of methane, ethane, and propane. The portion of the recycled overhead stream 52 that is not drawn from the middle portion of the distillation column 10 descends the distillation column 10 to join the liquid phase to become a bottoms stream 44. The bottoms stream 44 consists primarily of C3+ hydrocarbons and water, with minor amounts of carbon dioxide, methane, and ethane. In this embodiment, the pressure and temperature of the column are low enough to cause the water to freeze to water ice, thereby forming a solid phase separate from the C3+ liquid phase. The two phases are removed as a bottoms stream 44 and fed to a screw filter press 12 where the water ice stream 48 is separated from the liquid C3+ stream 46.

The liquid C3+ stream 46 is fed into a second distillation column where the liquid C3+ stream 46 is fractionally distilled to form a second overhead vapor stream 62 and a second bottoms liquid stream 56. In some embodiments, there is a middle fluid stream 59 drawn from the column from a middle portion. In other embodiments, this stream is empty. The second bottoms liquid stream 56 is passed through a reboiler, with a portion recycling as a second recycled bottoms stream 58 and the balance leaving as a C3+ product stream 60. The second overhead vapor stream 62 passes through a condenser, with a portion recycling as a second recycled overhead stream 64 and the balance moving on as a second product vapor stream 66. The second product vapor stream 66 consists primarily of carbon dioxide with minor amounts of methane, ethane, and propane. In a preferred embodiment, the second product vapor stream 66 is no more than 98 wt % carbon dioxide.

The product vapor stream 54 and the second product vapor stream 66 are passed into a desublimator 24. A natural gas liquid stream 78 is passed into the desublimator against the two product vapor streams. A portion of the natural gas liquid stream 78 vaporizes due to the drop in pressure and the enthalpy of vaporization is drawn from the carbon dioxide in the two product vapor streams, freezing the carbon dioxide to form a solid product stream 80. The solid product stream 80 contains a small amount of liquid ethane and liquid methane. The balance of the material in the desublimator 24 is now a vapor and is passed out as a first natural gas loop stream 68. The first natural gas loop stream 68, at substantially the same temperature as the natural gas liquid stream 78, is passed through a countercurrent heat exchanger 26 where it is warmed to form a second natural gas loop stream 70 which is compressed to form a third natural gas loop stream 72 which is cooled across heat exchanger 30 to form a cold natural gas loop stream 76. A portion of the cold natural gas loop stream 76 is drawn off as a natural gas product stream 74 while the balance is cooled across the exchanger 26 to form the natural gas liquid stream 78. In this embodiment, substantially the same temperature is preferably within 5° C. In a preferred embodiment, there is a cooling load in exchanger 26 to remove the heat of condensation from stream 76.

The solid product stream 80 is passed into a vessel 32 where it is warmed to drive off any liquid methane and ethane as secondary natural gas product stream 82, leaving dry solid product stream 84, which is pressed through an auger 34 into a melter 36. In a preferred embodiment, the pressure rise across the auger is about 10 bar. The pressure increase acts as a backpressure seal to prevent backward flow of liquids or vapors. The solid product stream is melted to form a liquid carbon dioxide stream 88, drawn from the melter by pump 38. In some embodiments, light gases that were trapped in the solid product stream 80 are removed from the melter as a light gas stream 89. In a preferred embodiment, stream 89 is empty.

In a preferred embodiment, the distillation column is made of stainless steel.

The invention has been described with reference to various specific and preferred embodiments and techniques. Nevertheless, it is understood that many variations and modifications may be made while remaining within the spirit and scope of the invention.

What is claimed is:

1. A method for separating components through a distillation column comprising:
    providing a process stream comprising hydrocarbons, carbon dioxide, and water;
    passing the process stream into the distillation column at a bottom portion of the distillation column;
    fractionally distilling the process stream in the distillation column forming an overhead vapor stream, a middle fluid stream, and a bottoms liquid stream;
    removing the middle fluid stream from a middle location of the distillation column;
    removing the bottoms liquid stream from the distillation column; and
    removing the overhead vapor stream from the distillation column;
    wherein the middle fluid stream comprises a first portion of the carbon dioxide and a first portion of the hydrocarbons; and
    wherein the bottoms liquid stream comprises a second portion of the hydrocarbons as a first phase and substantially all the water as a second phase.

2. The method of claim 1, wherein the process stream further comprises hydrogen sulfide, nitrogen, or combinations thereof.

3. The method of claim 1, wherein the process stream is a liquid and passing the process stream into the distillation column causes a portion of the liquid to flash to a vapor.

4. The method of claim 1, wherein the process stream is a mixture of a liquid phase and a vapor phase and passing the process stream into the distillation column directs the liquid phase to a reboiler and the vapor phase up the distillation column.

5. The method of claim 1, wherein the bottom portion of the distillation column is below all packing materials or trays.

6. The method of claim 1, further comprising physically separating the first phase and the second phase.

7. The method of claim 6, wherein the second phase is a solid.

8. The method of claim 7, wherein physically separating the first phase and the second phase comprises passing the bottoms liquid stream through a solid-liquid separator.

9. The method of claim 8, wherein the solid-liquid separator comprises a screw-filter press.

10. The method of claim 6, wherein a solvent is added to the process stream, the solvent being miscible and mixing with the second phase and depressing a freezing point of the second phase such that the water and the solvent are a liquid.

11. The method of claim 10, wherein the solvent is a water miscible polar molecule selected from the group consisting of alcohols, ketones, aldehydes, and combinations thereof.

12. The method of claim 10, wherein physically separating the first phase and the second phase comprises allowing the bottoms stream to gravity separate and removing the first phase by decanting the first phase from the second phase.

13. The method of claim 1, wherein the middle fluid stream is a liquid stream.

14. The method of claim 1, wherein the middle fluid stream is a gas stream.

15. The method of claim 1, wherein fractionally distilling the process stream in the distillation column further comprises operating a condenser at a top portion of the distillation column and a reboiler below the bottom portion of the distillation column.

16. The method of claim 15, wherein the condenser is operated within 5° C. above the freezing point of the overhead vapor stream.

17. The method of claim 1, wherein carbon dioxide is present in the middle fluid stream at a concentration of at least 98 wt % and contains at least 90 wt % of the carbon dioxide from the process stream.

18. The method of claim 1, wherein the process stream is passed into the distillation column above a required reboil temperature such that the distillation column acts as a rectifying column.

19. The method of claim 1, wherein the distillation column is a packed column.

20. The method of claim 1, further comprising maintaining the distillation column at a pressure at most 3 bar below supercritical pressure.

* * * * *